US008997590B2

(12) United States Patent
Oberdoerfer et al.

(10) Patent No.: US 8,997,590 B2
(45) Date of Patent: Apr. 7, 2015

(54) MULTI-PART MOUNTING DEVICE FOR AN ULTRASONIC TRANSDUCER

(75) Inventors: York Oberdoerfer, Langenfeld (DE); Judith Duerscheid, Huerth (DE); Jochen Zilz, Huerth (DE); Willi Warkowski, Kerpen (DE); Marek Parusel, Roesrath (DE)

(73) Assignee: GE Sensing & Inspection Technologies GmbH, Huerth (DE)

( * ) Notice: Subject to any disclaimer, the term of this patent is extended or adjusted under 35 U.S.C. 154(b) by 0 days.

(21) Appl. No.: 13/474,996

(22) Filed: May 18, 2012

(65) Prior Publication Data

US 2013/0019702 A1 Jan. 24, 2013

(30) Foreign Application Priority Data

May 20, 2011 (DE) .......................... 10 2011 076 224

(51) Int. Cl.
*G01N 29/22* (2006.01)
*G01N 29/26* (2006.01)
*G01N 29/27* (2006.01)
*G10K 11/00* (2006.01)

(52) U.S. Cl.
CPC .............. *G01N 29/223* (2013.01); *G01N 29/27* (2013.01); *G01N 29/262* (2013.01); *G10K 11/004* (2013.01); *G01N 2291/2634* (2013.01); *G01N 2291/263* (2013.01)

(58) Field of Classification Search
CPC .. H01L 41/053; H03H 9/0514; H03H 9/0538; H03H 9/0561

USPC ......... 310/322, 326, 327, 336, 348; 73/866.5, 73/432.1
See application file for complete search history.

(56) References Cited

U.S. PATENT DOCUMENTS

| | | | |
|---|---|---|---|
| 3,480,906 A * | 11/1969 | Thompson | 367/158 |
| 3,771,354 A * | 11/1973 | Miller | 73/639 |
| 5,125,411 A * | 6/1992 | Yokoi et al. | 600/463 |
| 6,222,897 B1 | 4/2001 | Hatley et al. | |
| 6,825,594 B1 * | 11/2004 | Thurn | 310/334 |
| 7,246,523 B2 * | 7/2007 | Magane et al. | 73/649 |
| 7,249,513 B1 * | 7/2007 | Zipparo et al. | 73/625 |
| 2003/0152745 A1 * | 8/2003 | Wagenblast | 428/119 |
| 2005/0043625 A1 * | 2/2005 | Oliver et al. | 600/459 |
| 2005/0043626 A1 * | 2/2005 | Marciante et al. | 600/459 |

OTHER PUBLICATIONS

European Search Report and Written Opinion issued in connection with corresponding EP Application No. 12168578.8-1559 dated Feb. 26, 2013.

* cited by examiner

*Primary Examiner* — Laura Martin
*Assistant Examiner* — Irving A Campbell
(74) *Attorney, Agent, or Firm* — GE Global Patent Operation; Mark A. Conklin

(57) ABSTRACT

A multi-part mounting device for an ultrasonic transducer, the mounting device comprising a first part configured to mount the mounting device on a housing of an ultrasonic test probe, and a second part configured to retain the ultrasonic transducer, wherein the second part is at least in touching contact with the ultrasonic transducer, wherein the second part comprises a first plastic and is connected by positive fit to the first part, and wherein the first part has a greater hardness than the second part.

17 Claims, 3 Drawing Sheets

MULTI-PART MOUNTING DEVICE FOR AN ULTRASONIC TRANSDUCER

BACKGROUND OF THE INVENTION

1. Field of the Invention

Embodiments of the present invention relate to a mounting device for an ultrasonic transducer on or in a probe housing and a generic ultrasonic testing device for a non-destructive inspection of a test object by ultrasound.

2. Description of the Prior Art

The principle of ultrasound inspection is known. It serves for finding casting defects or other material faults such as crack, pockets, piping or the like. The purpose of inspecting bar material is, in particular, to inspect internal defects, to examine surface defects, and to inspect the dimensions. Ultrasonic test probes comprise at least one transmitter that is excitable by electrical pulses for generating short ultrasonic pulses that are directed into the material to be inspected of a test object. Any defect in the material to be inspected, for example, a crack, a pocket or the like, causes an echo in the pulse, which is reflected back to the probe and is received by the transmitter, which in some cases simultaneously serves as a receiver. The reflected echo can also be received by a separate receiver of the test probe that is disposed adjacent to the transmitter. Measuring the delay in time between the original pulse and the return of the echo permits determination of the depth of the defect. The echo strength also permits, for example, displaying the size of the defect. Furthermore, defect determination with spatial resolution is also possible, but it requires a very exact positioning of the transducer that generates the ultrasound.

As a rule, such transducers, for example, one or more piezo oscillators such as piezoceramic elements, are disposed in a housing which is designed in a variety of ways, depending on the application. The housing and the ultrasonic transducer(s) are generally referred to as an ultrasonic test probe. The ultrasonic transducer is disposed in or on the housing in such a way that its ultrasound enters the test object to be inspected from a sound emitting surface of the transducer, generally through a coupling medium with a suitable thickness and acoustic impedance, such as water.

For example, a water area is provided and maintained between the ultrasonic transducer and the test object to be inspected, for example, a pipe or a bar. For this purpose, several techniques are known, such as inspection using an immersion technique, a puddle technique or a guided water jet. Furthermore, sealed water chambers with a test object passage, often referred to as SPS, is another known technique. After the test object has entered the sealed water chamber, the test object seals the chamber's inlet and outlet. The water chamber is filled with water in order to achieve the coupling between the test probe and the test object. Furthermore, rotary inspection devices are also known. A stable water jacket is generated by rotating the entire inspecting chamber including the test probes. Disposing sealing systems at the inlet and the outlet results in a substantially tubular water jacket through which the test objects can be conveyed.

However, the ultrasound or the ultrasonic pulse is not only emitted in the desired direction, but also in the opposite, direction. Due to the reflection of this rear-side pulse on boundary surfaces, the ultrasonic transducer receives unwanted ultrasound echoes that cause an interference or noise in the image in image-producing ultrasound inspection. This sound, which does not exit through the sound emitting surface, has to be directed away from the ultrasonic transducer and/or absorbed as efficiently as possible.

In order to accomplish this, the ultrasonic transducers are glued onto an acoustically damping material. This so-called backing material permits the ultrasonic waves emitted on the rear sides of the piezo element(s) to enter, couples them out by absorption or diffuse reflection, and thus prevents interferences. Thus, suitable backing materials exhibit as high an ultrasound absorption as possible and, on the other hand, have an acoustic impedance adapted to the ultrasonic transducer material, for example, the piezoceramics.

In order to achieve a high spatial resolution of the measurement, an exact and reproducible arrangement or mounting of the transducer in the housing, and, if applicable, also of the housing on the inspecting device, is desired. For example, it is important that the backing materials meet the processing-related requirements, such as surviving the thermal and mechanical manufacturing processes without any damage. In order to ensure the proper functioning of the transducer, the chemical compatibility of the materials in touching contact must be ensured, for example, for backing, piezoceramics, circuit board, glue and the like, wherein the materials used must not have a negative influence on each other, such as influencing the stability or processing properties; they should exhibit, for example, dimensional stability (even at higher temperatures) and result in a strongly adhesive bond together with the glues used.

A conventional single-part mounting device consists of lead oxide for mounting the transducer on a housing, wherein the lead material is supposed to both cause the mechanical connection with the housing as well as provide the acoustically damping property of the backing. Due to its toxicity, the use of lead oxide is questionable and, in some places, even legally prohibited. Other than lead oxide, the use of weakly cross-linked polymers as a backing material is also known. However, such backing materials frequently exhibit deficiencies in mechanical processing. The higher temperatures that occur during mechanical processing, curing and drying of adhesives, thermally and/or mechanically induced stresses cause deformations in the backing material. Since the backing materials cannot be mechanically processed, it is impossible to provide special fixing aids, such as fixing grooves, for local fixing of a transducer in a housing.

BRIEF SUMMARY OF THE INVENTION

According to an embodiment of the present invention, there is provided a multi-part mounting device for an ultrasonic transducer. The mounting device comprises a first part configured to mount the mounting device on a housing of an ultrasonic test probe, and a second part configured to retain the ultrasonic transducer, wherein the second part is at least in touching contact with the ultrasonic transducer, wherein the second part comprises a first plastic and is connected by positive fit to the first part, and wherein the first parts has a greater hardness than the second part.

According to another embodiment of the present invention, there is provided an ultrasonic test probe comprising at least one ultrasonic transducer, a housing and a multi-part mounting device. The multi-part mounting device comprises a first part configured to mount the mounting device on the housing of the ultrasonic test probe, and a second part configured to retain the ultrasonic transducer, wherein the second part is at least in touching contact with the ultrasonic transducer, wherein the second part comprises a first plastic and is connected by positive fit to the first part, and wherein the first part has a greater hardness than the second part.

According to another embodiment of the present invention, there is provided an ultrasonic testing device for ultrasound inspection of a test object. The ultrasonic testing device comprises at least one ultrasonic test probe comprising at least one ultrasonic transducer, a housing and a multi-part mounting device, an evaluation unit, and a mechanism for generating a relative movement between the at least one ultrasonic test probe and the test object. The multi-part mounting device comprises a first part configured to mount the mounting device on the housing of the ultrasonic test probe, and a second part configured to retain the ultrasonic transducer, wherein the second part is at least in touching contact with the ultrasonic transducer, wherein the second part comprises a first plastic and is connected by positive fit to the first part, and wherein the first part has a greater hardness than the second part.

BRIEF DESCRIPTION OF THE DRAWINGS

The advantages and implementation of embodiments of the present invention will become more apparent from the following examples described with reference to the drawings, wherein the drawings shall be understood as explanation of, rather than limitations to, embodiments of the present invention, wherein.

DETAILED DESCRIPTION OF THE INVENTION

Figure 1:
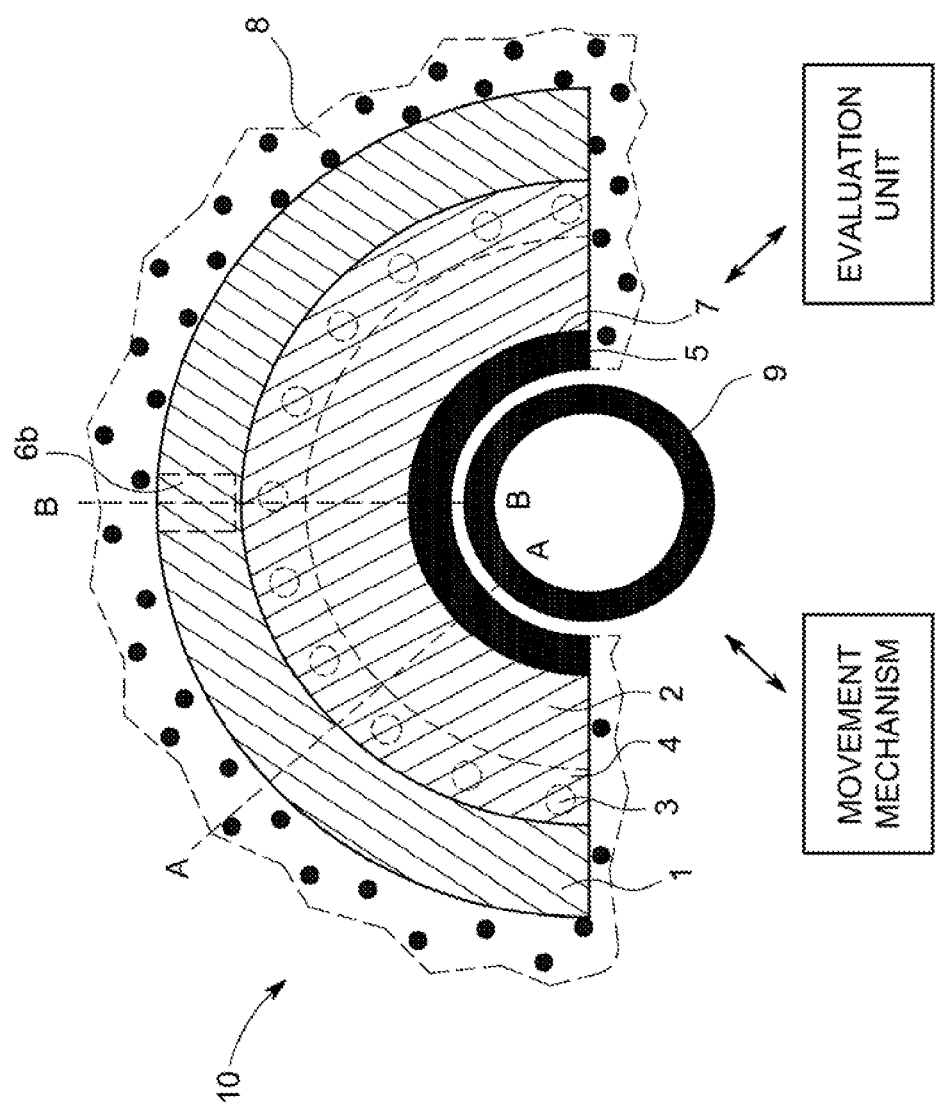
FIG. 1 shows a schematic view of a test probe with a tubular test object according to an embodiment of the present invention.

Embodiments of the present invention provide a mounting device for an ultrasonic transducer 5 which, on the one hand, meets acoustic requirements, such as damping and/or scattering of unwanted sound emission, and, on the other hand, also has a high mechanical strength and good dimensional stability.

It must be remarked that the embodiments cited individually in this disclosure can be combined in any technologically meaningful manner and depict other embodiments of the present invention. The description, in particular in connection with the figures, additionally characterizes and specifies embodiments of the present invention.

Embodiments of the present invention relate to a multi-part mounting device for an ultrasonic transducer 5. The term ultrasonic transducer 5 is to be construed broadly and comprises, for example, a single piezoceramic ultrasonic transducer (transceiver) as well as an arrangement of several transducers that can be controlled in a phased manner (phased array), such as 1.5D and 2D phased arrays. Furthermore, the mounting system according to an embodiment of the present invention is suitable also for transducers that have a plane sound-emitting surface, as well as transducers that have a curved sound-emitting surface. The mounting device according to an embodiment of the present invention comprises multiple parts, for example, at least a first part 1 for mounting on a housing 8 of an ultrasonic test probe 10, and a second part 2 which retains the ultrasonic transducer 5 and is at least in touching contact with the ultrasonic transducer 5. According to an embodiment of the present invention, the first part 1 has a greater hardness, in particular, Shore hardness, Vickers hardness and/or Rockwell hardness, than the second part 2.

The term housing 8 is to be construed broadly and does not require a design that wholly or partially encloses the transducer. For example, the housing 8 comprises a plate-shaped design.

In an embodiment, the first mechanically harder part 1 has a high level of stability, even under mechanical stress, and the second part 2, according an embodiment, is produced from a first plastic and takes on the acoustic task of the so-called backing, that is, the absorption and/or scattering of unwanted sound emission of the transducer 5.

According to an embodiment, the first part 1 and the second part 2 are connected by positive fit. Thus, the more acoustically active but more mechanically unstable material of the second part 2 is stabilized by the first part 1, wherein the first part 1, due to its hardness, provides the conditions for mechanical processing, such as machining, that is required for an exact position-retaining fixing of the transducer 5. The connection by positive fit between the two parts provides a secure connection. Furthermore, the plastic material of the second part 2 provides a good chemical compatibility for adhesives that are commonly used for mounting piezoceramics on the second part 2. Moreover, the thermal expansion coefficient of the second part 2 is in the order of magnitude of the thermal expansion coefficient of the piezoceramics used, so that stresses in the mutual connection are avoided. A person skilled in the art would be able to select the first plastic that is suitable, on the one hand, for chemical compatibility and, on the other hand, for the acoustic requirements.

In one embodiment, the first part 1 is substantially produced from a metallic and/or ceramic material and/or a second plastic with a greater hardness, in particular Shore hardness, than the first plastic. In another embodiment, it is entirely made from a metallic material.

According to another embodiment, in order to prevent a direct acoustic coupling between the housing 8 and the second part 2, the second part 2 is configured in such a way that it forms no contact with the housing 8 when the mounting device is mounted on the housing 8 of the ultrasonic test probe 10.

The connection by positive fit between the first part 1 and the second part 2 can be achieved, for example, by a tongue-and-groove connection. In one embodiment, the groove 6b is formed on the second part 2.

In one embodiment, in order to effect an effective acoustic damping and/or scattering action by the second part 2, the first part 1 is configured in such a way that the first part 1 has no contact with the ultrasonic transducer 5.

The first plastic used is, for example, a molded material consisting of a duroplastic. Duroplastic materials, which are also referred to as duromers, are plastics that are produced from hardenable resins. The duroplastic molded material provides the second part 2 with the required dimensional stability.

In one embodiment, the first plastic comprises at least one epoxy resin. In another embodiment, the first plastic comprises a bisphenol A epoxy resin. For example, this is a resin sold under the trade name "Araldit CY 221" to which the epoxy resin sold under the trade name "Araldit HY 956" has been added as a hardener.

The resin matrix of the second part 2 can contain a finely dispersed phase consisting of a polymer with a low glass transition temperature. Due to this polymer phase, the damping properties of the second part 2 are considerably improved while maintaining the good dimensional stability. In one embodiment, a silicone rubber (RTV) that cross-links at room temperature is added to the resin matrix. The damping action can be ascribed to a scattering action and reflection on the surface of the polymer phase or the silicone rubber, and consequently, the acoustic damping effect can be specifically adjusted. Because apart from the proportion and the particle size of the polymer phase or the silicone rubber in the resin matrix, interactions between the resin matrix and the polymer phase or the rubber also determine the quality of the damping action.

According to an embodiment of the present invention, the second part 2 has a sufficient acoustic impedance, such as an acoustic impedance adapted to the transducer material. The impedance can be adjusted by a suitable particle-shaped material, such as a material with a density that is high as compared with the plastic, being added to the material of the second part 2. In one embodiment, the suitable particle-shaped material is added to the material of the second part 2 at a proportion of up to about 50% by volume relative to the total material. In one embodiment, this additive, whose density is may be greater than or equal to about 3.5 g/cm$^3$, in particular greater than or equal to about 5 g/cm$^3$, is an inorganic filler such as tungstic oxide or, in another embodiment, bismuth oxide. $Bi_2O_3$. Other additives that can be used are, for example, aluminum oxide and lead-zirconium-titanate. In other embodiments, metallic powders, such as copper, silver and tungsten, can be used for increasing acoustic impedance if the additive is electrically conductive. In order to avoid sedimentation, particularly in the case of low-viscosity resin mixtures, additives known per se, such as pyrogenic silicic acid, may be added.

In one embodiment, the particle distribution of the filler has a D50 value in the range of approximately or exactly 1 µm to approximately or exactly 100 µm, while in another embodiment, in the range of approximately or exactly 10 µm to 50 µm, while in yet another embodiment, in the range of approximately or exactly 20 µm to approximately or exactly 30 µm. In one embodiment, the particle distribution of the filler has a D50 value of approximately or exactly 25 µm.

In one embodiment, the second part 2 is connected to the first part 1 by partially overmolding the latter. For example, the first part 1 is inserted into the die of a forming mold and partially overmolded with the plastic material of the second part 2.

According to another embodiment, the first part 1 comprises at least one opening 3 for mounting the second part 2. A durable connection is thus achieved between the first part 1 and the second part 2. It is thus accomplished that no separation of the first part 1 from the second part 2 occurs despite fracturing and/or crack formation in the plastic.

In one embodiment, the second part 2 and the first part 1 are configured to be at least ring-segment-shaped. For example, the first part 1 and second part 2 are configured in such a way that the inner boundary surface of the first part 1 defined by the inner radius is adjacent to the outer boundary surface of the second part 2 defined by the outer radius.

Embodiments of the present invention further relate to an ultrasonic test probe 10 comprising at least one ultrasonic transducer 5, a housing 8 and a multi-part mounting device in the previously described embodiments. The term ultrasonic transducer 5, as was mentioned above, is to be construed broadly and comprises, for example, a single piezoceramic ultrasonic transducer (transceiver) as well as an arrangement of several transducers that can be controlled in a phased manner (phased array), such as 1.5D and 2D phased arrays. Furthermore, the mounting system according to an embodiment of the present invention is suitable for transducers that have a plane sound-emitting surface, as well as transducers that have a curved sound-emitting surface. The mounting device according to an embodiment of the present invention comprises multiple parts, for example, at least a first harder part 1, which in one embodiment is a metallic part, for mounting on a housing 8 of an ultrasonic test probe 10, and a second softer part 2 which retains the ultrasonic transducer 5 and is at least in touching contact with the ultrasonic transducer 5. The term housing 8 is to be construed broadly and does not require a design that wholly or partially encloses the transducer 5. For example, the housing 8 comprises a plate-shaped design.

In order to locally fix the mounting device, and thus the ultrasonic transducer 5, in a reliable and reproducible manner, the housing 8 and the first part 1 form a fit, for example, an interference fit. In one embodiment, a guiding pin 6a is provided on the housing 8, which, during the installation of the mounting device on a housing 8, engages a guiding groove 6b of the first part 1 of the mounting device in a positive fit. The guiding groove 6b is, for example, inserted into the harder material of the first part 1 by machining.

In one embodiment, the transducer(s) 5 defines a curved or plane sound emitting surface facing a test object 9 to be inspected, and the second part 2 is disposed adjacent to the boundary surface 7 of the transducer(s) 5 which is opposite to the sound emitting surface. In one embodiment, the transducer 5 is glued to this second part 2.

Embodiments of the present invention further relate to an ultrasonic testing device for ultrasound inspection of a test object 9, for example, a pipe. The device comprises at least one ultrasonic test probe 10 according to one of the above-described embodiments, an evaluation unit, and means for generating a relative movement between the at least one ultrasonic test probe 10 and the test object 9. The ultrasonic testing device can comprise means for generating a relative movement between the test probe 10 and the test object 9 during and in between several inspections. According to other embodiments of the present invention, various techniques can be used for acoustic coupling between the test object 9 and the test probe 10, such as an immersion technique, a puddle technique, using a guided water jet. A sealed water chamber with a test object passage (SPS) and rotary inspection devices may also be utilized.

Figure 2:
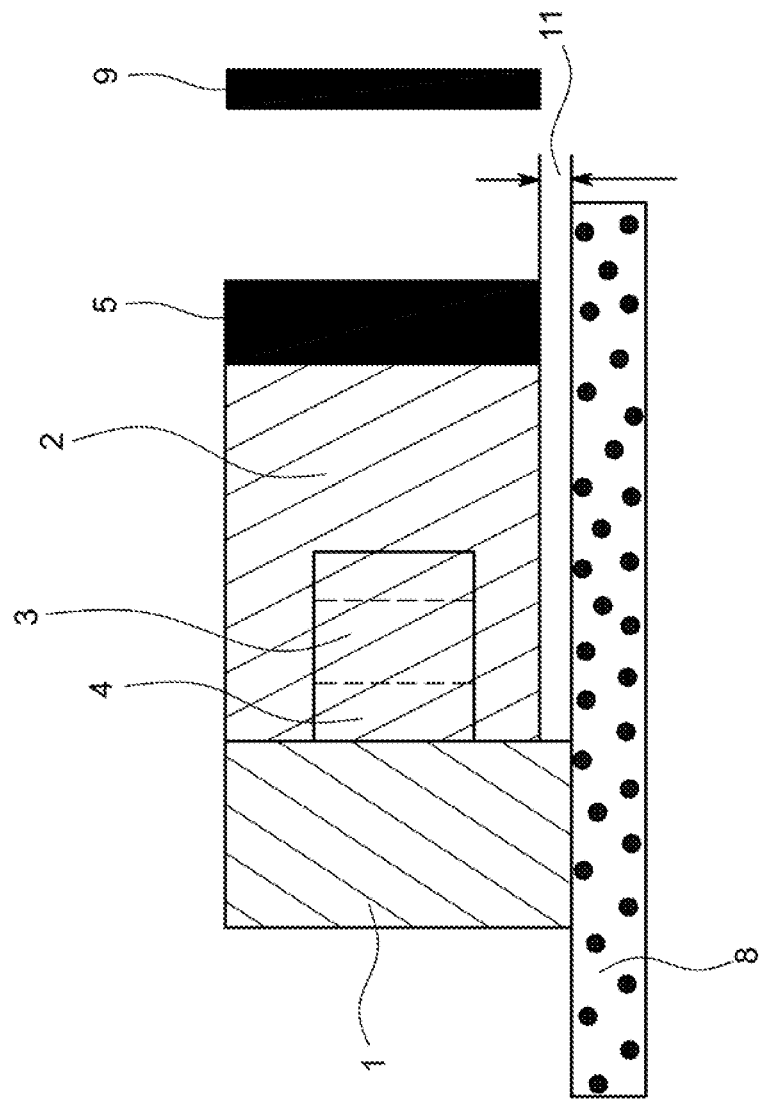
FIG. 2 shows a sectional view taken along section line AA of FIG. 1 according to an embodiment of the present invention.
Figure 3:
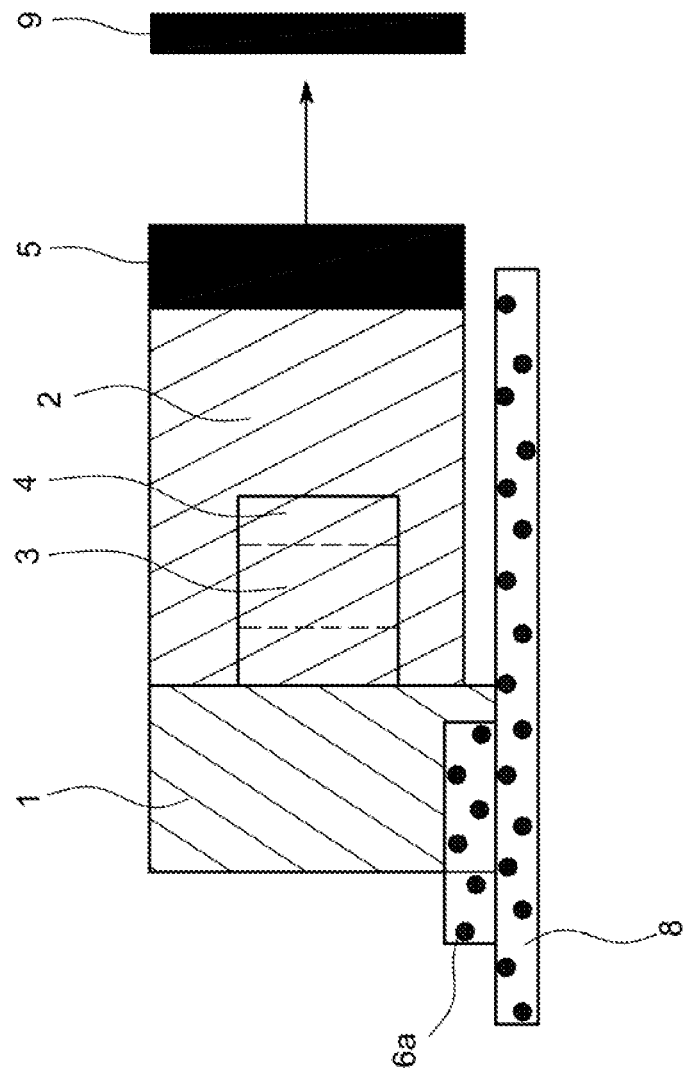
FIG. 3 shows a sectional view taken along section line BB of FIG. 1 according to an embodiment of the present invention.

FIG. 1 is a schematic view of a test probe 10 according to an embodiment of the present invention. The test probe 10 provides non-destructive inspection by ultrasound of a test object 9, which in FIG. 1 is a pipe. A half-ring-shaped ultrasonic transducer 5 is connected to a housing 8 through a two-part mounting device, with the housing 8 being depicted only in parts. The half-ring-shaped ultrasonic transducer 5 is glued to the second part 2 of the mounting device. The second part 2, which is illustrated as the inner part of the mounting device in FIG. 1, is capable of absorbing the radially acting contact forces required during gluing due to its curved shape. The mounting device comprises two concentrically disposed, half-ring-shaped parts connected by positive fit; a first part 1 and the second part 2 described above. The first part 1, which is illustrated as the outer part of the mounting device in FIG. 1, may be metallic. The second part 2 is produced from an epoxy resin composition comprising Araldit CY 221 and Araldit HY 956 as a hardener. The epoxy resin composition comprises as a filler bismuth oxide powder (D50=about 25 µm) and a ground and screened mixture of glass fibers and silicone rubber cross-linked at room temperature. The weight ratios are about 60:12:500:30. The connection by positive fit between the first part 1 and the second part 2 is accomplished by inserting the first part 1 into a die and the resin, which is flowable prior to hardening, being introduced into the die in order to form the second part 2 after hardening. In the process, the second part 2 encloses the annular projection 4 formed on the first part 1 and penetrates the openings 3 formed in the projection 4. Thus, the first part 1 and the second part 2 form a positive tongue-and-groove connection, with the projection 4 of the first part 1 being embedded into the groove of the second part 2. The mechanically processable first part 1 serves for installation of the mounting device on the housing 8. As illustrated, the mounting on the housing 8 comprises a fit of a groove 6b formed on the first part 1, into which a pin 6a on the housing 8 latches. A reproducible local fixing of the mounting device, and thus of the transducer 5, on the housing 8 is thus achieved. As shown in FIG. 2, the second part 2 is configured in such a way that, upon mounting the first part 1 on the housing 8, the second part 2 forms a gap 11 between the second part 2 and the housing 8. Therefore, the inner part 2 is not in contact with the housing 8.

What is claimed is:

1. A multi-part mounting device for an ultrasonic transducer, the mounting device comprising:
   a first part configured to mount the mounting device on a housing of an ultrasonic test probe, the housing comprising a planar surface upon which to mount the first part; and
   a second part configured to retain the ultrasonic transducer, wherein the second part comprises a first side that is at least in touching contact with the ultrasonic transducer,
   wherein the second part comprises a first plastic and is connected by positive fit to abut the first part,
   wherein the second part comprises a second side opposite the first side, the second side comprising the positive fit to abut the first part,
   wherein the first part has a greater hardness than the second part,
   wherein the positive fit comprises a projection extending from the first part and embedded into the second part, and
   wherein the projection comprises an opening, and wherein the first plastic of the second part is disposed through the opening, and surrounds and abuts the projection.

2. The multi-part mounting device according to claim 1, wherein the first part comprises at least one of a metallic, a ceramic material and a second plastic, wherein the second plastic has a greater hardness than the first plastic.

3. The multi-part mounting device according to claim 1, wherein the first part is not in contact with the ultrasonic transducer.

4. The multi-part mounting device according to claim 1, wherein the second part is connected to the first part by partially overmolding the first part.

5. The multi-part mounting device according to claim 1, wherein a projection of the second part is configured to be mounted to a groove of the first part.

6. The multi-part mounting device according to claim 1, wherein the second part and the first part are configured to be ring-segment-shaped.

7. The multi-part mounting device according to claim 1, wherein the projection is perpendicular to a first surface of the first part, and wherein the first surface of the first part is perpendicular to the planar surface of the housing.

8. The multi-part mounting device according to claim 7, wherein the first surface of the second part is perpendicular to the planar surface of the housing.

9. An ultrasonic test probe comprising at least one ultrasonic transducer, a housing and a multi-part mounting device, wherein the multi-part mounting device comprises:
   a first part comprising a first side and a second side perpendicular to the first side, the first side of the first part adjoining the housing and the second side extending perpendicularly away from the housing, the first side of the first part configured to mount the mounting device on the housing of the ultrasonic test probe; and
   a second part configured to retain the ultrasonic transducer, the second part comprising a first side and a second side opposite the first side, wherein the first side of the second part is at least in touching contact with the ultrasonic transducer,
   wherein the second part comprises a first plastic, and the second side of the second part is connected by positive fit to the second side of the first part,
   wherein the positive fit comprises a projection extending from the first part and embedded into the second part,
   wherein the projection comprises an opening, and wherein the first plastic of the second part is disposed through the opening, and surrounds and abuts the projection, and
   wherein the first part has a greater hardness than the second part.

10. The ultrasonic test probe according to claim 9, wherein the housing and the first part form a fit, and wherein the first part is at least in touching contact with the housing.

11. The ultrasonic test probe according to claim 10, wherein the housing comprises a guiding pin and the first part comprises a guiding groove, and wherein the guiding pin engages the guiding groove to form the fit between the housing and the first part.

12. The ultrasonic test probe according to claim 9, further comprising a transceiver or a phased array.

13. The ultrasonic test probe according to claim 9, wherein the at least one ultrasonic transducer comprises:
   a curved or plane sound emitting surface facing a test object to be inspected; and
   a boundary surface opposite the curved or plane sound emitting surface,
   wherein the first side of the second part is disposed adjacent to the boundary surface.

14. The ultrasonic test probe according to claim 9, wherein the second part comprises a third side between the first and second sides of the second part, and wherein the third side is parallel to and spaced apart from the housing.

15. An ultrasonic testing device for ultrasound inspection of a test object, the ultrasonic testing device comprising:
   at least one ultrasonic test probe comprising at least one ultrasonic transducer, a housing and a multi-part mounting device, wherein the multi-part mounting device comprises:
      a first part comprising a first side and a second side perpendicular to the first side, the first side of the first part adjoining the housing and the second side extending perpendicularly away from the housing, the first side of the first part configured to mount the mounting device on the housing of the ultrasonic test probe; and
      a second part configured to retain the ultrasonic transducer, the second part comprising a first side and a second side opposite the first side, wherein the first side of the second part is at least in touching contact with the ultrasonic transducer,
      wherein the second part comprises a first plastic and the second side of the second part is connected by positive fit to the second side of the first part,
      wherein the positive fit comprises a projection extending from the first part and embedded into the second part,
      wherein the projection comprises an opening, and wherein the first plastic of the second part is disposed through the opening, and surrounds and abuts the projection, and
      wherein the first part has a greater hardness than the second part;

an evaluation unit; and a mechanism for generating a relative movement between the at least one ultrasonic test probe and the test object.

16. The ultrasonic testing device of claim 15, wherein the housing comprises a guiding pin and the first part comprises a guiding groove, and wherein the guiding pin engages the guiding groove.

17. The ultrasonic testing device of claim 16, wherein the first side of the first part comprises a projection embedded into the second part to form the positive fit.

* * * * *